(12) United States Patent
Bergeron, Jr.

(10) Patent No.: US 6,274,630 B1
(45) Date of Patent: Aug. 14, 2001

(54) METHOD OF INHIBITING BIOSYNTHESIS OF EIF5A

(75) Inventor: Raymond J. Bergeron, Jr., Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 08/928,492

(22) Filed: Sep. 12, 1997

Related U.S. Application Data

(60) Provisional application No. 60/025,896, filed on Sep. 13, 1996.

(51) Int. Cl.$^7$ .................................................... A61K 31/13
(52) U.S. Cl. ......................... 514/667; 514/256; 514/668; 514/669; 514/670; 514/674
(58) Field of Search .................................... 514/256, 667, 514/668, 669, 670, 674

(56) References Cited

U.S. PATENT DOCUMENTS 5,091,576 * 2/1992 Bergeron .............................. 564/361

\* cited by examiner

*Primary Examiner*—Frederick Krass
(74) *Attorney, Agent, or Firm*—Miles & Stockbridge; Dennis P. Clarke

(57) ABSTRACT

A method and pharmaceutical composition for inhibiting or preventing the intracellular biosynthesis of EIf5A by the administration to a human or non-human mammal in need thereof an amount of a polyamine analogue or salt thereof sufficient to deplete the supply of intracellular spermidine required for EIf5A biosynthesis.

5 Claims, 6 Drawing Sheets

METHOD OF INHIBITING BIOSYNTHESIS OF EIF5A

RELATED APPLICATION

Reference is hereby made to U.S. Provisional Patent Application Ser. No. 60/025,896 filed Sep. 13, 1996, the benefit of the filling date of which is claimed herein.

BACKGROUND OF THE INVENTION

The initiation factor, EIf5A, is unique in that it is the only known cellular protein that contains the amino acid hypusine (Hpu) [$N_\epsilon$-(4-amino-2-hydroxybutyl)lysine], an unusual naturally occurring amino acid, having the structure:

(A)

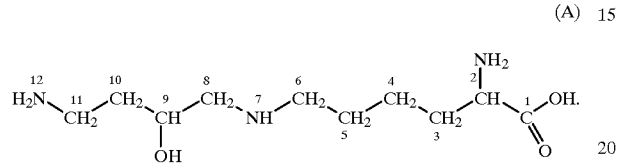

Hypusine was first isolated from bovine brain extracts by Shiba et al in 1971 [Biochim. Biophys. Acta., Vol. 244, pages 523–531 (1971)]. The molecule has two chiral centers at positions 2 and 9, each of which can be classified R or S by the Cahn-Ingold-Prelog method. The post-translational formation of the (2S, 9R) diastereomer:

(B)

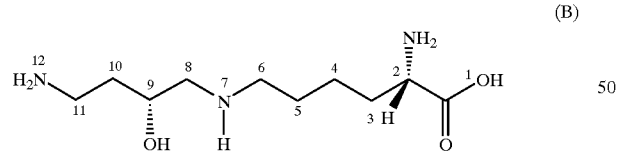

has been shown to occur on a precursor protein of the eukaryotic initiation factor 5A, i.e., EIf5A (formerly called eIF-4D) [Cooper et al, *Proc. Natl. Acad. Sci. U.S.A.*, Vol. 80, pages 1854–1857 (1983); and Safer, *Eur. J. Biochem.*, Vol. 186, pages 1–3 (1989)].

EIf5A is biosynthesized by the post-translational aminobutylation of lys-51 of the precursor polypeptide followed by hydroxylation which results in hypusine at residue 51. In the mid-1970's, EIf5A was shown to stimulate ribosomal subunit joining and to enhance 80 S-bound Met-t-RNAi reactivity with puromycin [Anderson et al, *FEBS Lett.*, Vol. 76, pages 1–10 (1977); and Kemper et al, *J. Biol. Chem.*, Vol. 251, pages 5551–5557 (1976)]. Later in 1983, Cooper et al, supra, suggested that a hypusine-modified protein serves as an important 1–5 initiation factor in all growing eukaryotic cells. In 1986, Park et al [*J. Biol. Chem.*, Vol. 261, pages 14515–14519 (1986)] isolated the EIf5A protein from human red blood cells and elucidated the amino acid sequence surrounding the single hypusine residue, as Thr-Gly-Hpu-His-Gly-His-Ala-Lys. EIf5A has also been found to be essential to HIV replication [Bevec et al, *J. Proc. Natl. Acad. Sci. U.S.A.*, Vol. 91, pages 10829–10833 (1994); and Ruhl et al, *J. Cell Biol.*, Vol. 123, pages 1309–1320 (1994)].

The initial step in the biosynthesis of EIf5A in the cell requires spermidine as the aminobutyl donor.

It is an object of the present invention to provide a method of inhibiting or preventing intracellular biosynthesis of EIf5A.

SUMMARY OF THE INVENTION

The above and other objects are realized by the present invention, one embodiment of which relates to a method for the inhibition or prevention of the intracellular biosynthesis of EIf5A comprising administering to a human or non-human mammal in need thereof an amount of a polyamine sufficient to deplete the supply of intracellular spermidine required for EIf5A biosynthesis, the polyamine having one of the formulae:

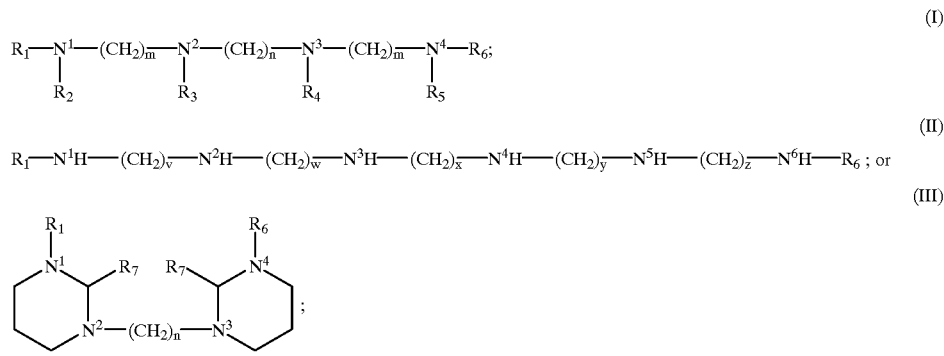

wherein: $R_1$ and $R_6$ may be the same or different and are H, alkyl or aralkyl having from 1 to 12 carbon atoms, provided that, in formula (I), $R_1$ and $R_6$ are not H;

$R_2$–$R_5$ may be the same or different and are H, $R_1$ or $R_6$;

$R_7$ is H, alkyl, aryl or aralkyl having from 1 to 12 carbon atoms;

m is an integer from 3 to 6, inclusive;

n is an integer from 3 to 6, inclusive;

v, w, x, y and z may be the same or different and are integers from 3 to 10, inclusive;

(IV)

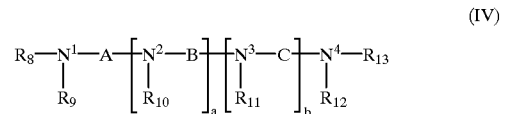

or its possible stereoisomers wherein:

$R_8$–$R_{13}$ may be the same or different and are alkyl, branched alkyl, aryl, arylalkyl, cycloalkyl, optionally having an alkyl chain interrupted by at least one etheric oxygen atom, or hydrogen;

$N^1$, $N^2$, $N^3$ and $N^4$ are nitrogen atoms capable of protonation at physiological pH's;

a and b may be the same or different and are integers from 1 to 4, with the proviso that one, but not both, of a and b may be 0;

A, B and C may be the same or different and are bridging groups which effectively maintain the distance between the nitrogen atoms such that the polyamine:

(i) is capable of uptake by a target cell upon administration of the polyamine to a human or non-human mammal or is capable of binding to at least one polyamine site of a receptor located within or on the surface of a cell upon administration of the polyamine to a human or non-human mammal; and (ii) upon uptake by the target cell, competitively binds via an electrostatic interaction between the positively charged nitrogen atoms to biological counteranions;

the polyamine, upon binding to the biological counter-anion in the cell, functions in a manner biologically different than the intracellular polyamines; and further wherein at least one of said bridging groups A, B and C may contain at least one —CH(OH)— group which is not alpha- to either of the nitrogen atoms; or (V) a salt thereof with a pharmaceutically acceptable acid.

Another embodiment of the invention comprises a pharmaceutical composition comprising an amount of a polyamine sufficient, upon administration to a human or non-human mammal in need thereof, to deplete the supply of intracellular spermidine required for EIf5A biosynthesis in the mammal, and a pharmaceutically acceptable carrier therefor, the polyamine having one of the formulae:

(I)

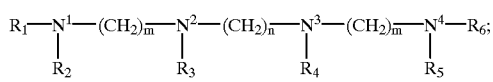

(II)

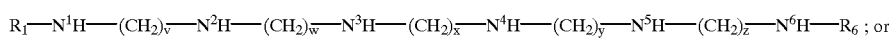; or (III)

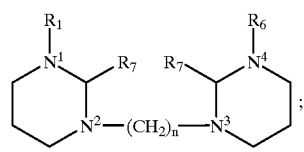

wherein: $R_1$ and $R_6$ may be the same or different and are H, alkyl or aralkyl having from 1 to 12 carbon atoms, provided that, in formula (I), $R_1$ and $R_6$ are not H;

$R_2$–$R_5$ may be the same or different and are H, $R_1$ or $R_6$;

$R_7$ is H, alkyl, aryl or aralkyl having from 1 to 12 carbon atoms;

m is an integer from 3 to 6, inclusive;

n is an integer from 3 to 6, inclusive;

v, w, x, y and z may be the same or different and are integers from 3 to 10, inclusive;

(IV)

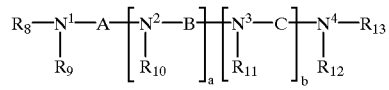

or its possible stereoisomers wherein:

$R_8$–$R_{13}$ may be the same or different and are alkyl, branched alkyl, aryl, arylalkyl, cycloalkyl, optionally having an alkyl chain interrupted by at least one etheric oxygen atom, or hydrogen;

$N^1$, $N^2$, $N^3$ and $N^4$ are nitrogen atoms capable of protonation at physiological pH's;

a and b may be the same or different and are integers from 1 to 4, with the proviso that one, but not both, of a and b may be 0;

A, B and C may be the same or different and are bridging groups which effectively maintain the distance between the nitrogen atoms such that the polyamine:

(i) is capable of uptake by a target cell upon administration of the polyamine to a human or non-human mammal or is capable of binding to at least one polyamine site of a receptor located within or on the surface of a cell upon administration of the polyamine to a human or non-human mammal; and (ii) upon uptake by the target cell, competitively binds via an electrostatic interaction between the positively charged nitrogen atoms to biological counter-anions;

the polyamine, upon binding to the biological counter-anion in the cell, functions in a manner biologically different than the intracellular polyamines; and further wherein at least one of said bridging groups A, B and C may contain at least one —CH(OH)— group which is not alpha- to either of the nitrogen atoms; or (V) a salt thereof with a pharmaceutically acceptable acid.

DETAILED DESCRIPTION OF THE INVENTION

Figure 1:
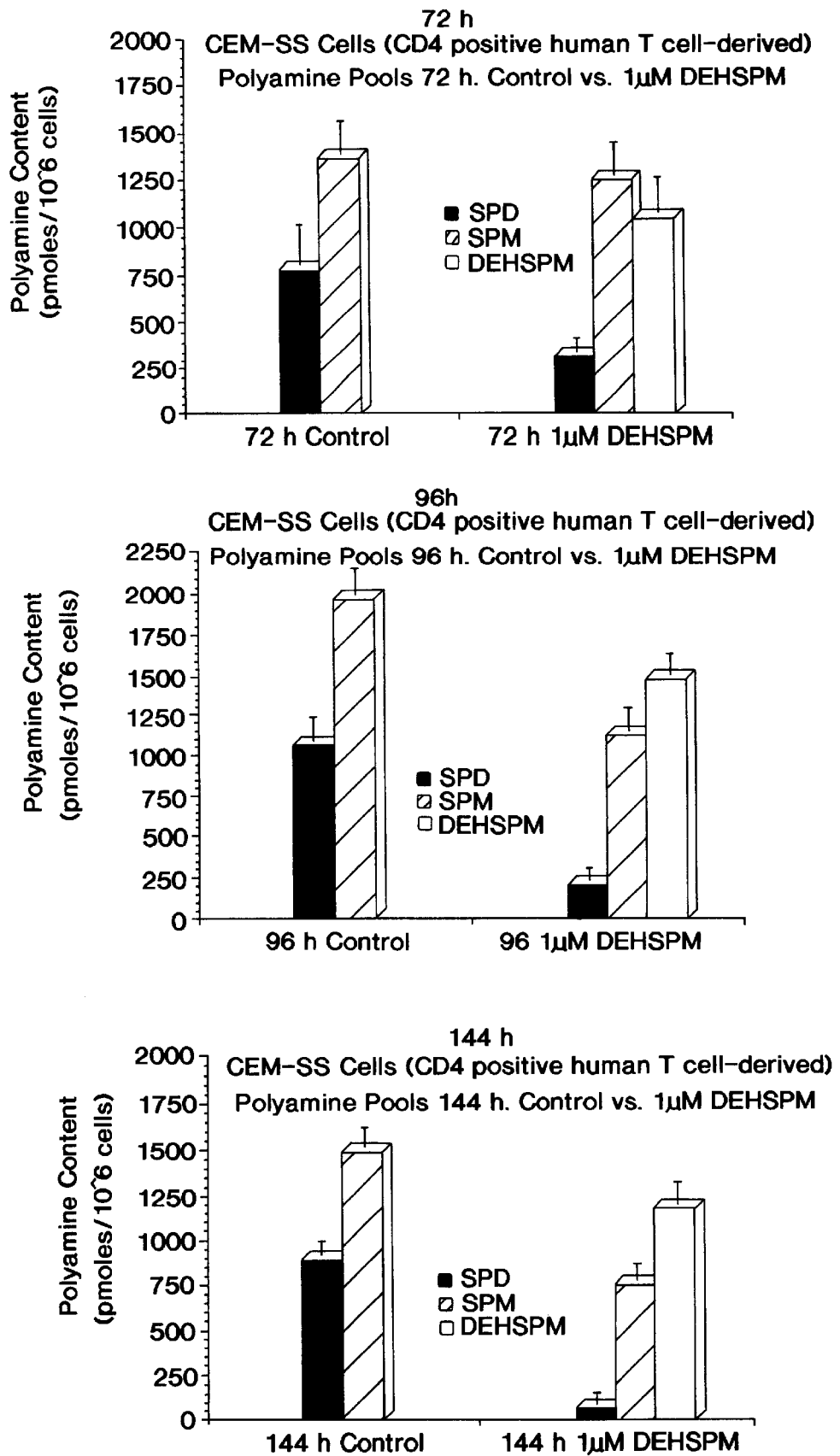
FIGS. 1–6 are graphic depictions of the results obtained from employing the composition of the invention in the method of the invention.

The present invention is predicated on the discovery that polyamines of the above formulae, when administered to human or non-human mammals, suppress the intracellular biosynthesis of spermidine by depleting the cell of the enzymes ornithine decarboxylase (ODC) and S-adenosylmethionine decarboxylase (AdoMetDC), thereby depleting the supply of intracellular spermidine available to initiate synthesis of EIf5A. As a result, depending on the dosage of polyamine administered, the amount of intracellular EIf5A produced may be severely limited or eliminated.

In the polyamines of formula (IV), the bridging groups A, B and C may be the same or different and are preferably alkyl, branched alkyl, cycloalkyl, arylalkyl or a heterocyclic bridging group wherein at least one of said $N^1$, $N^2$, $N^3$ or $N^4$ atoms is incorporated in the ring as a hetero atom.

Suitable polyamines for use in the compositions and methods of the present invention having the formulae (I), (II), (III) and (IV) above, as well as derivatives and salts thereof (V), are those described in U.S. Pat. Nos. 5,091,576; 5,393,757; and 5,510,390, the entire contents and disclosures of each of which are incorporated herein by reference. Methods for the preparation of the polyamines are also disclosed therein. Hydroxy-substituted polyamines suitable for use in the methods and compositions of the invention and methods for their production are described in U.S. patent application Ser. No. 08/595,877 filed Feb. 6, 1996, now U.S. Pat. No. 5,962,533 the entire contents and disclosures of which are incorporated herein by reference.

It will be understood that those skilled in the art, given the disclosure herein of the invention, will be able to determine, without the exercise of undue experimentation, the dosage of polyamine necessary to reduce the intracellular production of EIf5A to a desired level in any particular application while not severely disrupting intracellular polyamine homeostasis. Generally, dosages in the range of from about 5 to about 200 mg/m$^2$ will be sufficient.

It will be appreciated that while the agents described above form acid addition salts and carboxy acid salts, the biological activity thereof will reside in the agent itself. These salts may be used in human medicine and presented as pharmaceutical formulations in the manner and in the amounts (calculated as the base) described herein, and it is then preferable that the acid moiety be pharmacologically and pharmaceutically acceptable to the recipient. Examples of such suitable acids include (a) mineral acids, i.e., hydrochloric, hydrobromic, phosphoric, metaphosphoric and sulfuric acids; (b) organic acids, i.e., tartaric, acetic, citric, malic, lactic, fumaric, benzoic, glycolic, gluconic, gulonic, succinic and aryl-sulfonic acids, e.g., p-toluenesulfonic acid.

The pharmaceutical compositions of the invention preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally. The active ingredients may be admixed or compounded with any conventional, pharmaceutically acceptable carrier or excipient. It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in *Remington's Pharmaceutical Sciences*, 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

The therapeutically effective amount of active agent to be included in the pharmaceutical composition of the invention depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg.

While it is possible for the agents to be administered as the raw substances, it is preferable, in view of their potency, to present them as a pharmaceutical formulation. The formulations of the present invention for human use comprise the agent, together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives, such as methyl hydroxybenzoate, chlorocresol, metacresol, phenol and benzalkonium chloride. Such materials are of special value when the formulations are presented in multidose containers.

Buffers may also be included to provide a suitable pH value for the formulation. Suitable such materials include sodium phosphate and acetate. Sodium chloride or glycerin may be used to render a formulation isotonic with the blood. If desired, the formulation may be filled into the containers under an inert atmosphere such as nitrogen or may contain an anti-oxidant, and are conveniently presented in unit dose or multi-dose form, for example, in a sealed ampoule.

The invention is illustrated by the following non limiting examples.

EXAMPLE 1

The CEM-SS cell line derived from a human T4-lymphoblastoid line was chosen as a test model because it is CD4 positive and is susceptible to infection with HIV. The cells were treated with a 1 µm dose of diethylhomospermine that resulted in only a mild inhibition of cell growth, i.e., a concentration estimated to result in only 25% growth inhibition ($IC_{75}$).

Figure 2:
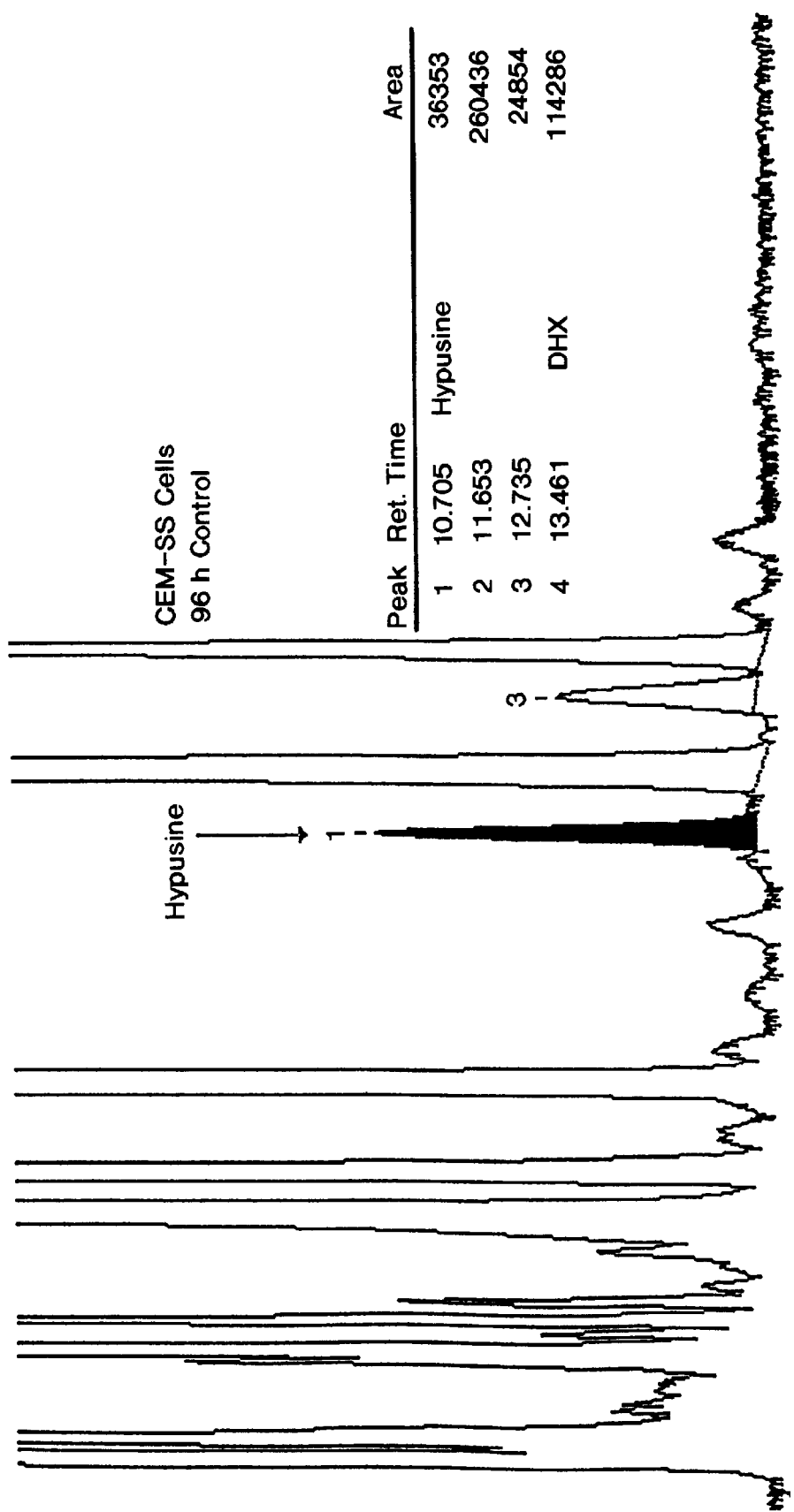
Figure 3:
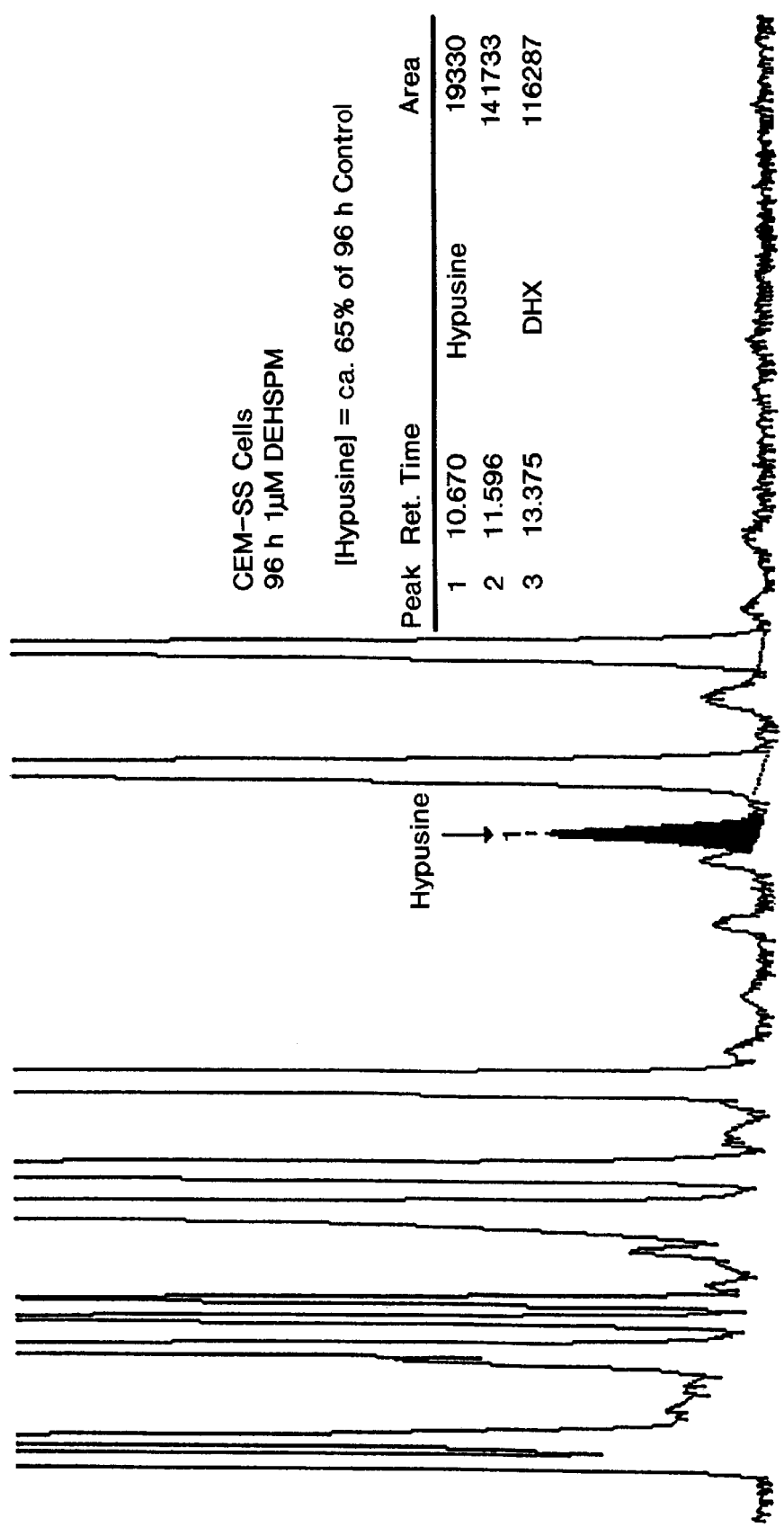
Figure 4:
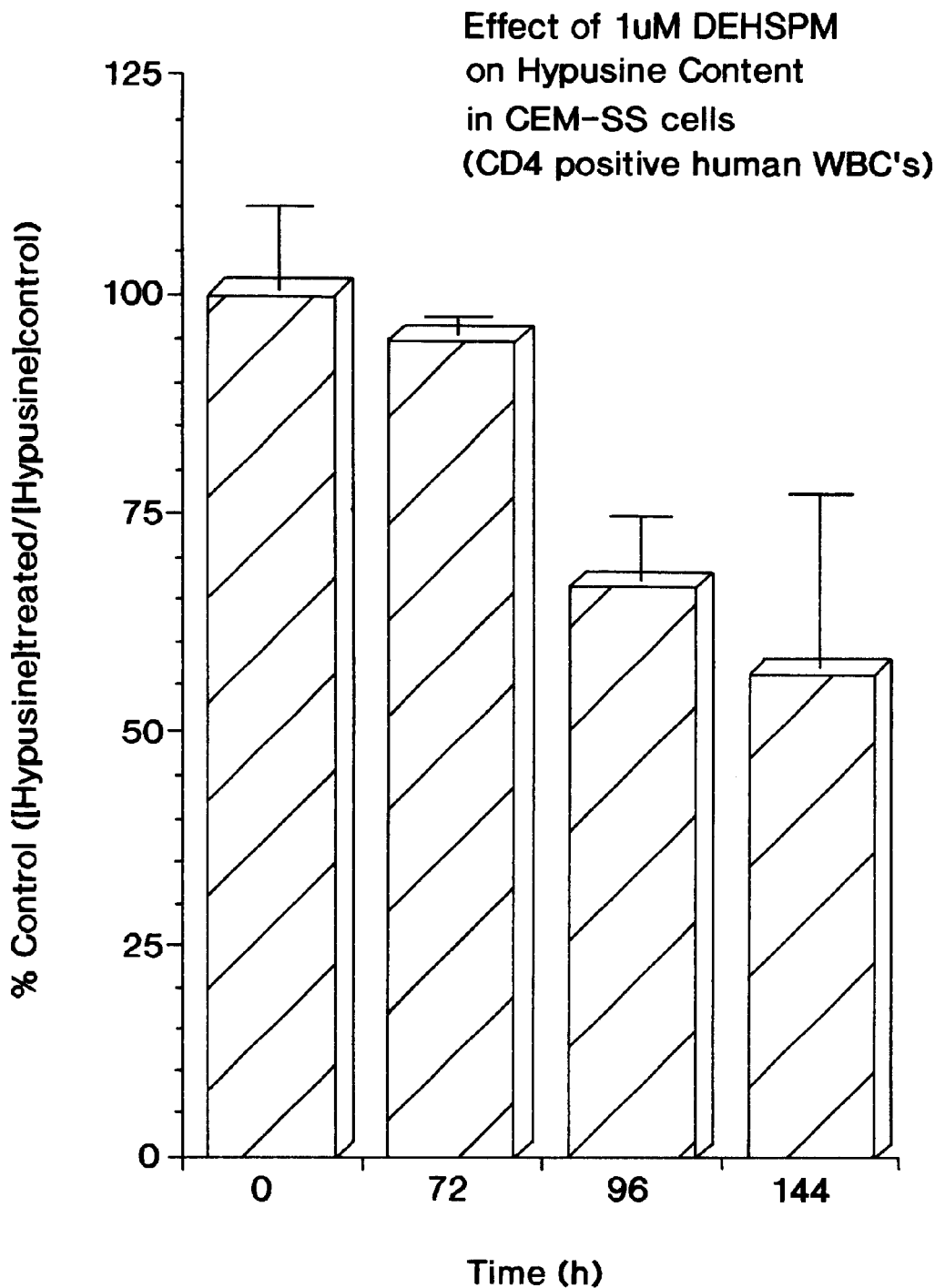

The results over 72-hour, 96-hour and 144-hour treatment programs are set forth graphically in FIG. 1 which shows the decrease in the levels of spermidine (SPD) and spermine (SPM) in the cell line as a result of treatment with diethylhomospermine (DEHSPM). The results of the 96-hour treatment on the levels of hypusine in the cell line are set forth in FIG. 2 (control) and FIG. 3. The reduced level of hypusine reflects the decreased production of EIf5A in the cells as a result of treatment with diethylhomospermine. FIG. 4 shows the effect on the levels of hypusine in the cell line after 72, 96 and 144 hours of treatment with diethylhomospermine.

EXAMPLE 2

Several human patients were selected for a five (5) day protocol of treatment with diethylnorspermine. Polyamine levels [spermidine (SPD), diethylnorspermine (DENSPM) and hypusine (Hpu)] were measured on day one and used as pretreatment controls. Each patient then received the drug for five days and a second sample was taken. In several cases, samples were taken in the middle of the dosing schedule. The dose is contained in the first column of the following table under "Patient." For example, "1–094" means this patient received a dose of 94 mg/m² once per day for five days; "1–118" means this patient received a dose of 118 mg/m² once per day for five days, etc. The polyamine levels were again determined on day five. The results are set forth in the following table.

TABLE

| Patient | Day# | SPD | DENSPM | Hypusine | Fraction Control△ |
|---|---|---|---|---|---|
| 1-094 | Monday | 93 | 0 | 72011 | |
| 1-094 | Friday | 91 | 176 | 26400 | 0.367 |
| 1-094 | Monday | 441 | 0 | 25200 | |
| 1-094 | Friday | 242 | 31 | 17730 | 0.704 |
| 2-094 | Monday | 230 | 0 | 11952 | |
| 2-094 | Friday | 192 | 136 | 7811 | 0.654* |
| 3-094 | Monday | 576 | 38 | 20603 | |
| 3-094 | Friday | 107 | 102 | 13927 | 0.676* |
| 1-118 | Wednesday | 248 | 34 | 26056 | |
| 1-118 | Friday | 196 | 59 | 7487 | 0.287** |
| 1-118 | Wednesday | 510 | 85 | 31408 | |
| 1-118 | Friday | 184 | 108 | 17558 | 0.559** |
| 1-148 | Monday | 426 | 0 | 29621 | |
| 1-148 | Friday | 311 | 168 | 13540 | 0.457 |
| 1-185 | Monday | 349 | 0 | 78414 | |
| 1-185 | Wednesday | 376 | 181 | 35525 | 0.453 |
| 1-185 | Friday | 50 | 276 | 36565 | 0.466 |

Monday = First day of a five-day course of treatment ending on subsequent Friday; thus, Monday = pre-treatment "control."
△Ideally, "fraction of control" compares Friday [Hypusine] with a "control" [Hypusine] from the previous Monday.
*Represents a comparison of a Friday [Hypusine] with a different Monday sample from the same patient.
**Represents a comparison of Friday sample to the Wednesday sample of the same week.

As can be seen from the results set forth in the foregoing table, the levels of spermidine were lowered in each patient's cell line, resulting in a decreased production of EIf5A as demonstrated by the reduced levels of hypusine in each case.

Figure 5:
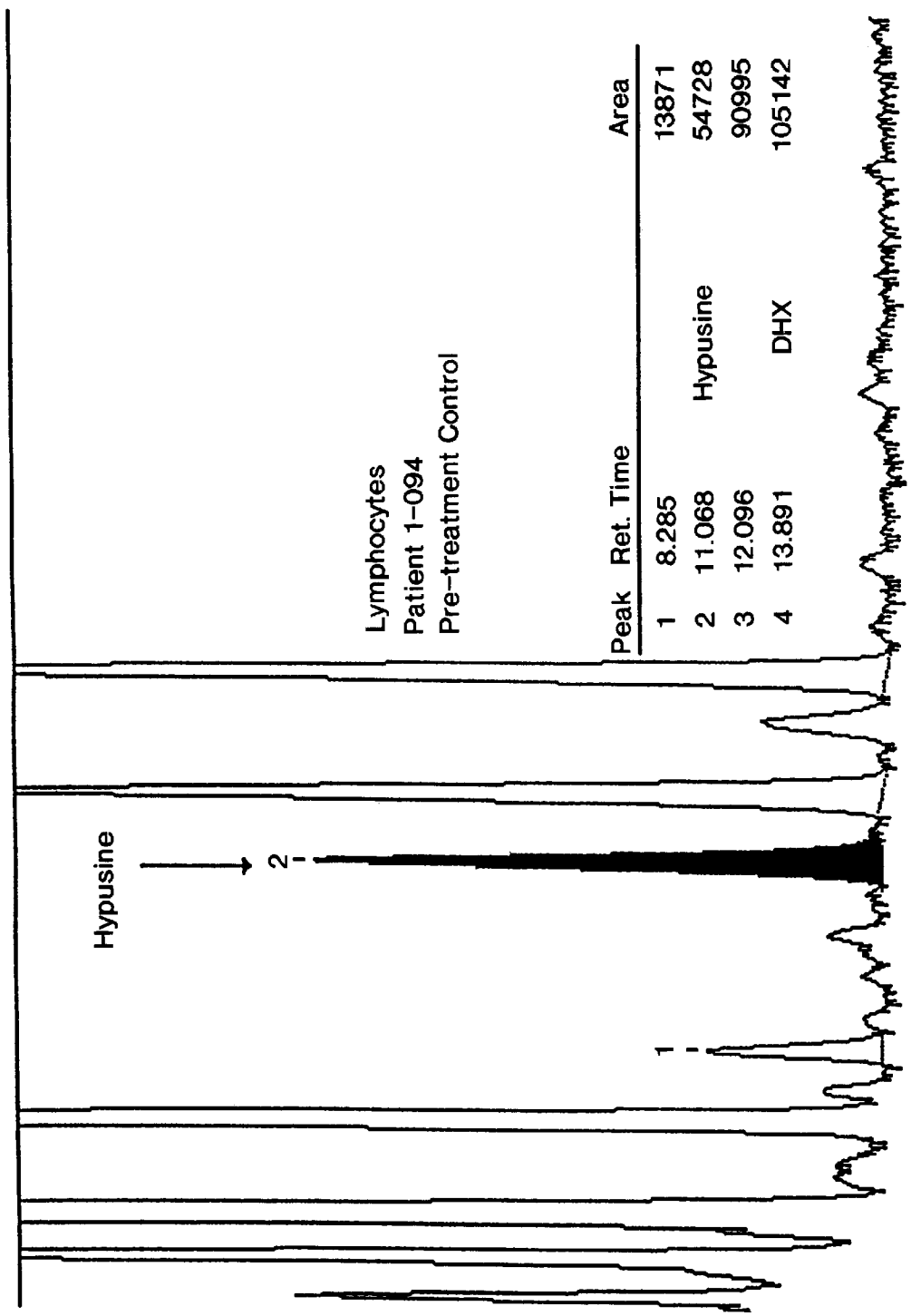
Figure 6:
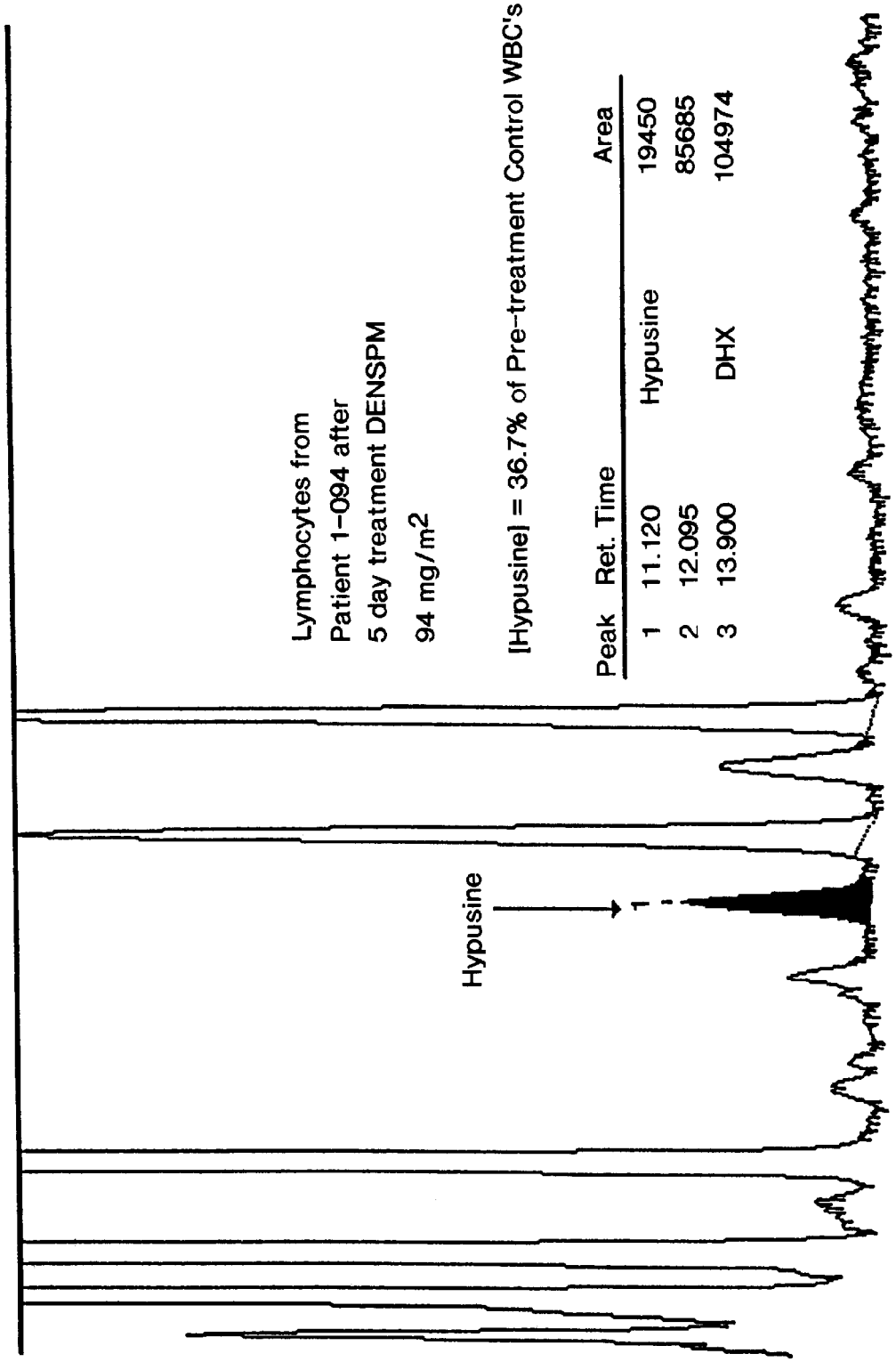

The results for hypusine levels in patient 1–094 are graphically depicted in FIG. 5 [hypusine level on day Monday (control)] and FIG. 6 [hypusine level on day Friday (after treatment)].

I claim:
1. A method for the inhibition or prevention of the intracellular biosynthesis of ElfSA comprising administering to a human or non-human mammal in need thereof an amount of a polyamine sufficient to deplete the supply of intracellular spermidine required for Elf5A biosynthesis, but insufficient to substantially affect polyamine homeostasis, said polyamine having one of the formulae:

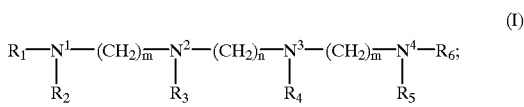

(I)

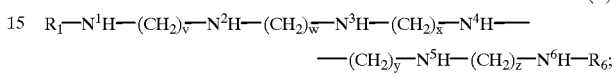

(II)

or

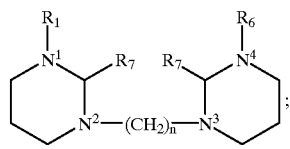

(III)

wherein: $R_1$ and $R_6$ may be the same or different and are H, alkyl or aralkyl having from 1 to 12 carbon atoms, provided that, in formula (I), $R_1$ and $R_6$ are not H;
$R_2$–$R_5$ may be the same or different and are H, $R_1$ or $R_6$;
$R_7$ is H, alkyl, aryl or aralkyl having from 1 to 12 carbon atoms;
m is an integer from 3 to 6, inclusive;
n is an integer from 3 to 6, inclusive;
v, w, x, y and z may be the same or different and are integers from 3 to 10, inclusive;

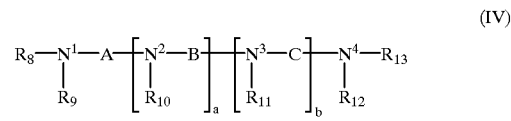

(IV)

or its stereoisomers wherein:
$R_8$–$R_{13}$ may be the same or different and are alkyl, branched alkyl, aryl, arylalkyl, cycloalkyl, optionally having an alkyl chain interrupted by at least one etheric oxygen atom, or hydrogen;
$N^1$, $N^2$, $N^3$ and $N^4$ are nitrogen atoms capable of protonation at physiological pH's;
a and b may be the same or different and are integers from 1 to 4, with the proviso that one, but not both, of a and b may be 0;
A, B and C may be the same or different and are bridging groups which effectively maintain the distance between the nitrogen atoms such that the polyamine:
(i) is capable of uptake by a target cell upon administration of the polyamine to a human or non-human mammal or is capable of binding to at least one polyamine site of a receptor located within or on the surface of a cell upon administration of the polyamine to a human or non-human mammal; and
(ii) upon uptake by the target cell, competitively binds via an electrostatic interaction between the positively charged nitrogen atoms to biological counter-anions;

the polyamine, upon binding to the biological counter-anion in the cell, functions in a manner substantially biologically different than the intracellular polyamines; and further wherein at least one of said bridging groups A, B and C may contain at least one —CH(OH)— group which is not alpha- to either of the nitrogen atoms; or (V) a salt thereof with a pharmaceutically acceptable acid.

2. The method of claim 1 wherein said polyamine is diethylhomospermine.

3. The method of claim 1 wherein said polyamine is diethylnorspermine.

4. The method of claim 1 wherein said polyamine is administered to a human.

5. The method of claim 1 wherein the amount of polyamine administered is from about 5 to about 200 mg/m$^2$.

* * * * *